United States Patent [19]

Murgita

[11] Patent Number: 5,384,250
[45] Date of Patent: Jan. 24, 1995

[54] EXPRESSION AND PURIFICATION OF CLONED ALPHA-FETOPROTEIN

[75] Inventor: Robert A. Murgita, Montreal, Canada

[73] Assignee: McGill University, Montreal, Canada

[21] Appl. No.: 133,773

[22] Filed: Oct. 8, 1993

Related U.S. Application Data

[63] Continuation of Ser. No. 767,435, Sep. 27, 1991, abandoned.

[51] Int. Cl.$^6$ ............ C12P 21/06; A61K 35/14; C12N 15/00
[52] U.S. Cl. .................. 435/69.6; 435/69.1; 530/350; 530/380; 536/23.5
[58] Field of Search ........... 530/324, 350, 363, 380; 435/69.1, 69.7, 69.6; 536/23.5

[56] References Cited

U.S. PATENT DOCUMENTS 5,206,153  4/1993  Tamaoki et al. .................. 435/69.7

FOREIGN PATENT DOCUMENTS 2005866  1/1990  Japan .

OTHER PUBLICATIONS

Sambrook, et al. *Molecular Cloning*, 1989, pp. 17.37–17.43.
Innis et al., Arch. Biochem. Biophys 195:128, 1979.
Moringa et al., Proc. Natl. Acad. Sci. USA 80:4604, 1983.
Boismenu et al., Life Sciences 43:673, 1988.
Nishi et al., J. Biochem. 104:968 (1988).
Giuliani et al., Protein Engineering 2:605 (1989).
Yamamoto et al., Life Sciences 46:1679, (1990).

*Primary Examiner*—Robert A. Wax
*Assistant Examiner*—Keith D. Hendricks
*Attorney, Agent, or Firm*—Fish & Richardson

[57] ABSTRACT

In general, the invention features a method for producing human alpha-fetoprotein in prokaryctic cells. The method includes: providing a transformed prokaryotic cell including a recombinant DNA molecule encoding human alpha-fetoprotein operably linked to sequence elements capable of directing expression of alpha-fetoprotein, and permitting the transformed cell to express human alpha-fetoprotein.

4 Claims, No Drawings

EXPRESSION AND PURIFICATION OF CLONED ALPHA-FETOPROTEIN

This is a continuation of application Ser. No. 07/767,435, filed Sep. 27, 1991, now abandoned.

BACKGROUND OF THE INVENTION

The field of the invention is expression and purification of cloned human alpha-fetoprotein.

Alpha-fetoprotein (AFP) is a serum protein normally found at significant levels only in fetal blood. In adult blood increased alpha-fetoprotein levels are associated with liver regeneration and certain carcinomas.

The specific function of alpha-fetoprotein is not known. Suggested roles for the protein include: fetal albumin; protection from maternal immune attack; and protection from maternal estrogen.

Morinaga et al. (Proc. Natl. Acad. Sci. USA 80:4604, 1983) report the cloning of human AFP.

Innis et al. (Arch. Biochem. Biophys. 195:128, 1979) report the cloning of an approximately 950 base-pair fragment of human AFP into E. coli plasmid pBR322.

Nishi et al. (J. Biochem. 104:968, 1988) report the expression of rat AFP in E. Coli and Saccharomyces cerevisiae. Nishi et al. also report that, in an estradiol-binding assay, yeast-produced rat rAFP is as active a authentic AFP, while bacterial-produced rat rAFP is essentially inactive. Further, when characterized by radioimmunoassay or an Ouchterlony double immunodiffusion assay, yeast-produced rat rAFP bears a closer resemblance to authentic rat AFP than does bacterial-produced rat rAFP. Nishi et al. state that:

"In the Ouchterlony double immunodiffusion test, authentic and yeast rAFP formed a completely fused precipitin line with antibody to rat AFP while E. coli rAFP showed a reaction of partial identity in a similar test . . . . It is likely that the functionally active yeast rAFP in this study had the correct pairs of disulfide bridges. On the other hand the E. coli rAFP probably failed to form them".

Yamamoto et al. (Life Sciences 46:1679, 1990) report the expression of human AFP in yeast and report that the rAFP so produced was "indistinguishable immunologically from authentic AFP."

Giuliani et al. (Protein Engineering 2:605, 1989) report the expression of a portion of human AFP (amino acids 38 to 119) in E. coli.

Japanese Patent Application 88158596 reports a method for preparing recombinant human domain I AFP in E. coli.

SUMMARY OF THE INVENTION

In general, the invention features a method for producing human alpha-fetoprotein in a prokaryotic cell. The method includes providing a transformed prokaryotic cell that includes a recombinant DNA molecule encoding human alpha-fetoprotein operably linked to an expression control element capable of directing expression of human alpha-fetoprotein, and permitting the transformed cell to express human alpha-fetoprotein. In a preferred embodiment, the prokaryotic cell is E. coli. In more preferred embodiments, the expression control element includes an E. coli Trp promoter and the expression control element includes an E. coli Tac promoter.

In a related aspect, the invention features substantially pure human alpha-fetoprotein produced by providing a transformed prokaryotic cell that includes a recombinant DNA molecule encoding human alpha-fetoprotein operably linked to an expression control element capable of directing expression of human alpha-fetoprotein, and permitting the transformed cell to express human alpha-fetoprotein.

In a related aspect, the invention features a therapeutic composition comprising substantially pure alpha-fetoprotein produced as described above.

By "human alpha-fetoprotein" is meant a polypeptide having substantially the same amino acid sequence as the protein encoded by the human alpha-fetoprotein gene. Moringa et al. (Proc. Natl. Acad. Sci. USA 80:4604, 1983) reports the sequence of cDNA complementary to human alpha-fetoprotein.

By "expression control element" is meant a nucleotide sequence which includes recognition sequences for factors that control expression of a protein coding sequence to which it is operably linked. Accordingly, an expression control elememnt generally includes sequences for controlling both transcription and translation, for example, promoters, ribosome binding sites, repressor binding sites, and activator binding sites.

By "substantially the same amino acid sequence" is meant a polypeptide that exhibits at least 80% homology with naturally occurring amino acid sequence of human alpha-fetoprotein, typically at least about 85% homology with the natural human alpha-fetoprotein sequence, more typically at least about 90% homology, usually at least about 95% homology, and more usually at least about 97% homology with the natural human alsph-fetoprotein sequence. The length of comparison sequences will generally be at least 16 amino acids, usually at least 20 amino acids, more usually at least 25 amino acids, typically at least 30 amino acids, and preferably more than 35 amino acids.

Homology, for polypeptides, is typically measured using sequence analysis software (e.g., Sequence Analysis Software Package of the Genetics Computer Group, University of Wisconsin Biotechnology Center, 1710 University Avenue, Madison, Wis. 53705). Protein analysis software matches similar sequences by assigning degrees of homology to various substitutions, deletions, substitutions, and other modifications. Conservative substitutions typically include substitutions within the following groups: glycine alanine; valine, isoleucine, leucine; aspartic acid, glutamic acid, asparagine, glutamine; serine, threonine; lysine, arginine; and phenylalanine, tyrosine.

As used herein, the term "substantially pure" describes a protein or polypeptide which has been separated from components which naturally accompany it. Typically, a protein of interest is substantially pure when at least 60% to 75% of the total protein in a sample is the protein of interest. Minor variants or chemical modifications typically share the same polypeptide sequence. A substantially pure protein will typically comprise over about 85 to 90% of the protein in sample, more usually will comprise at least about 95%, and preferably will be over about 99% pure. Normally, purity is measured on a chromatography column, polyacrylamide gel, or by HPLC analysis.

A protein is substantially free of naturally associated components when it is separated from the native contaminants which accompany it in its natural state. Thus, a protein which is chemically synthesized or produced in a cellular system different from the cell from which it naturally originates will be substantially free from its naturally associated components. Thus the term can be used to describe polypeptides and nucleic acids derived from eukaryotic organisms which have been synthesized in *E. coli* and other prokaryotes.

The present invention provides for substantially pure human alpha-fetoprotein. Various methods for the isolation of human AFP from biological material may be devised, based in part upon the structural and functional properties of human alpha-fetoprotein. Alternatively, anti-AFP antibodies may immobilized on a solid substrate to generate a highly specific affinity column for purification of human AFP.

Besides substantially full-length polypeptides, the present invention provides for biologically active recombinant fragments of alpha-fetoprotein. For example, fragments active in ligand binding or immunosuppression.

The natural or synthetic DNA fragments coding for human alpha-fetoprotein or a desired fragment thereof will be incorporated into DNA constructs capable of introduction to and expression in cell culture. DNA constructs prepared for introduction into such hosts will typically include an origin of replication which can be utilized by the host cell, a DNA fragment encoding the desired portion of human alpha-fetoprotein, transcription and translational initiation regulatory sequences operably linked to the alpha-fetoprotein encoding segment, and transcriptional and translational termination regulatory sequences operably linked to the alpha-fetoprotein encoding segment. The transcriptional regulatory sequences will typically include a heterologous promoter which is recognized by the host. The selection of an appropriate promoter will depend upon the host, but promoters such as the trp, tac and phage promoters, tRNA promoters and glycolytic enzyme promoters may be used under appropriate circumstances (Sambrook et al. eds., Molecular Cloning: Laboratory Manual, Cold Spring Harbor Press, Cold Spring Harbor, N.Y. 1989). In some instances it may be desirable to include appropriately positioned recognition sequences for factors capable of regulating transcription in the host cell (e.g., the lac repressor of *E. coli*). Commercially available expression vectors, which include the replication system and transcriptional and translational regulatory sequences together with convenient sites for the insertion of a DNA fragment encoding the gene to be expressed may be used.

The various promoters, transcriptional, and traslational described above are generally referred to as an "expression control element".

It is also possible to integrate a DNA fragment encoding all or part of human AFP into the host cell's chromosome.

The vectors containing the DNA segments of interest can be transferred into the host cell by well-known methods, which vary depending on the type of cellular host (Sambrook et al., supra). The term "transformed cell" is meant to also include the progeny of a transformed cell.

Prokaryotic hosts useful for high level expression of recombinant proteins include: various strains of *E. coli*, *Bacillus subtilis*, and Pseudomonas.

The method of the invention provides a means by which to generate large quantities of human alpha-fetoprotein having biological activity. AFP produced according to the method of the invention has biological activity despite the fact that it is not modified in the same fashion as naturally occurring human AFP.

Other features and advantages of the invention will be apparent from the following description of the preferred embodiments thereof, and from the claims.

DETAILED DESCRIPTION

Construction of a cDNA Library

A cDNA library was constructed with size-fractionated cDNA (0.5–3 kb) prepared from poly(A)+ RNA isolated from liver cells (~3 grams wet weight) of a 4.5 months old human abortus. (Alternatively, a fetal cDNA library may be obtained from Clontech Laboratories, Inc., Palo Alto, Calif.) Total RNA was prepared by the guanidium thiocyanate method (Chirgwin et al., Biochemistry 18:5294, 1979), and mRNA was selected by oligo(dT)-cellulose chromatography (Collaborative Research, Bedford, Mass.) (Current Protocols in Molecular Biology, Ausubel et al., eds., Wiley Interscience, New York, 1989). cDNA was synthesized using the Librarian II cDNA synthesis kit (Invitrogen, San Diego, Calif.) and fractionated on a 1% agarose gel. Fragments of 0.5 to 3 kb were extracted and ligated to vector pTZ18-RB (Invitrogen), and used to transform competent *E. coli* DH1αF' (Invitrogen). Colony lifts were performed with Colony/Plaque Screen filters (DuPont, Wilmington, Del.), and the transferred bacterial colonies were lysed and denatured by incubation in a solution of 0.5M NaOH, 1.5M NaCl for 10 min. The filters were washed for 5 min in 1.5M NaCl, 0.50M Tris-HCl (pH 7.6), and air dried. Filters were then washed 5 times in chloroform, soaked in 0.3M NaCl to remove cellular debris, and then air dried. The DNA was fixed to the nitrocellulose by baking at 80° under vacuum for 2 hrs. The baked filters were prehybridized for 3 hr at 37° C. in 6×SSC (1×SSC=150 mM NaCl, 15 mM sodium citrate [pH 7.0]), 1×Denhardt's solution (0.2 g/l polyvinylpyrrolidone, 0.2 g/l BSA, 0.2 g/l Ficoll 400), 0.05% sodium pyrophosphate, 0.5% SDS, and 100 μg/ml *E. coli* DNA. Hybridization was performed for 18–24 hr at 37° C. in the same solution without SDS, containing 1–2×10$^6$ cpm/ml of two oligonucleotides $^{32}$P-labelled by 5'-end phosphorylation (Current Protocols in Molecular Biology, supra). The sequence of the oligonucleotides used for probing the library: 5'-TGTCTGCAGGATGGGGAAAAA-3' (SEQ ID NO: 1) and 5'-CATGAAATGACTCCAGTA-3' (SEQ ID NO: 2), correspond to positions 772 to 792 and positions 1405 to 1422 of the human AFP coding sequence respectively. Filters were washed twice for 30 min at 37° C. with 6X SSC, 0.05% sodium pyrophosphate and once for 30 min at 48° C. in the same solution. Dried filters were exposed to Kodak XAR films in the presence of Du Pont Cronex Lightning Plus intensifier screens for 24–48 hr to identify positive clones. Positive clones were isolated, amplified, and subjected to Southern blot analysis (Current Protocols in Molecular Biology, supra). Briefly, purified DNA was hydrolyzed with the appropriate restriction enzymes, and the resulting fragments were resolved on a 1% agarose gel. The DNA was then transferred to a nitrocellulose membrane. Hybridization conditions were as described above except that a third $^{32}$p-labelled oligonucleotide (5'-CATAGAAATGAATATGGA-3' (SEQ ID NO: 3), representing positions 7 to 24 of the human AFP coding region) was used in addition to the other two probes described above. Five positive clones were identified among the 3,000 colonies screened. One clone, pLHuAFP, was used in the construction described below.

Construction of Full Length Human AFP cDNA

A construct containing a translation initiation codon followed by the human AFP coding sequence and a translation termination codon was created using the following five DNA fragments.

Fragment 1: Two unphosphorylated oligonucleotides were annealed to form a double-stranded DNA molecule consisting of a 5'-end cohesive EcoRI recognition site, followed by an ATG initiation codon and the first 60 bp of the human AFP cDNA up to and including the PstI restriction site located at position 60 in the coding sequence (In this scheme, nucleotide 1 is the first nucleotide of the first codon (Thr) in the mature protein and corresponds to nucleotide 102 of Morinaga et al., supra). This fragment was ligated to pUC119 (pUC19 with the intergenic region of M13 from HgiA I at 5465 to AhaII at 5941 inserted at the Nde I site of pUC19) linearized with Eco RI and Pst I. The resulting DNA was amplified in *E. coli* NM522 (Pharmacia, Piscataway, N.J.) The EcoRI-PstI insert was recovered by enzymatic digestion of the recombinant plasmid followed by electrophoretic separation on a 5% polyacrylamide gel and isolation from the gel.

Fragment 2: A 97 bp human AFP cDNA fragment (positions 57 to 153) was obtained by digesting pLHuAFP with PstI and NsiI and gel purifying as described above. This clone contains the entire coding region of human AFP as well as 5' and 3' untranslated sequences.

Fragment 3: A 224 bp human AFP cDNA fragment (positions 150 to 373) was obtained by digesting pLHuAFP with NsiI and AlwNI and purifying as described above. Fragment 4: A 1322 bp human AFP cDNA fragment (positions 371 to 1692) was obtained by digesting pLHuAFP with AlwNI and StyI and purifying as described above.

Fragment 5: Two unphosphorylated oligonucleotides were annealed to form a 86 bp double-stranded DNA contains the human AFP sequence from position 1693 in the StyI site to the TAA termination codon that ends the AFP coding region at position 1773, followed by a cohesive BamHI site. This synthetic DNA was used without any further manipulations.

pBlueScript (StrataGene, La Jolla, Calif.) was completely hydrolyzed with EcoRI and BamHI, and added to ligation mixture containing the five purified fragments described above. A control ligation contained only the linearized pBluescript. Portions of these two ligation mixtures were used to transform competent *E. coli* DH5α (GIBCO/BRL, Grand Island, N.Y.). Recombinant plasmids were isolated from several transformants and screened by extensive restriction enzyme analysis and DNA sequencing. One recombinant plasmid was selected and termed pHuAFP. It was used for subsequent insertion of the human AFP gene into several expression vectors. pHuAFP includes a unique EcoRI-BamHI fragment that contains the complete coding sequence for human AFP in addition to an ATG start codon at the 5'-end and a TAA stop codon at the 3'-end.

AFP Expression Vectors

Successful high-level synthesis of human AFP in *E. coli* was achieved in three different expression systems. The TRP system gave direct expression. The RX1 system yielded a fusion protein containing 20 amino acids encoded by trpE and vector sequences. The MAL system expressed AFP fused to the male gene product, a 42 kd maltose-binding protein.

TRP Expression System: The 1186 bp EcoRI-BamHI AFP encoding fragment of pHuAFP was cloned into the expression vector pTrp4 (Olsen et al., J. Biotechnol. 9:179, 1989) downstream of the trp promoter and a modified ribosome-binding site.

Briefly, pHuAFP was digested with EcoRI and BamHI, and the ends were filled using Klenow polymerase. The 1186 bp AFP fragment was then gel purified. pTRp4 was ClaI digested, the ends were filled using Klenow polymerase, and the linearized vector was gel purified. The 1186 bp AFP fragment and pTrp4 backbone were ligated and used to transform competent *E. coli* of the following strains: DH5α, BL21 (F. W. Studier, Brookhaven National Laboratory, Upton, N.Y.), SG927 (American Type Culture Collection, Rockville, Md.: Acc. No. 39627), SG928 (ATCC Acc. No. 39628), and SG935 (ATCC Acc. No. 39623).

RX1 Expression System: Human AFP cDNA was cloned into the expression vector pRX1 (Rimm et al., Gene 75:323, 1989) adjacent to the trp promoter and in the translation frame of TrpE. The human AFP cDNA was excised from pHuAFP by digestion with EcoRI and BamHI and cloned into suitably treated pRX1 (BioRad Laboratories, Hercules, Calif.). The *E. coli* strains described above and CAG456 (D. W. Cleveland, Johns Hopkins University, Baltimore, Md.) were then transformed with the final plasmid construction identified as pRX1/HuAFP.

MAL Expression System: AFP cDNA was into inserted in the expression vector pMAL (New England Biolabs, Inc., Beverly, Mass.) under control of the tac promoter and in the translation frame of MalE. Briefly, pHuAFP was hydrolysed with BamHI and the ends made blunt using Klenow polymerase. The human AFP cDNA was released from the rest of the plasmid DNA by EcoRI digestion and then gel purified. The purified fragment was ligated to appropriately digested pMAL-C. A correctly oriented recombinant plasmid, designated pMAL/HUAFP, was used to transform *E. coli* DH5α, TBI (New England Biolabs) and SG935.

The AFP coding region used in the construction of the three expression vectors was sequenced and found to encode full length AFP.

Expression of AFP in *E. coli*

Bacterial cultures were incubated at 30° C. or 37° C. with aeration. Overnight cultures of *E. coli* were grown in LB medium supplemented with the appropriate antibiotics as required (Tetracycline-HCl was at 50 μg/ml, and ampicillin-Na was at 100 μg/ml).

TRP and RX1 Expression Systems: The trp promoter was induced under tryptophan starvation conditions. Induction was performed in M9CA medium prepared as follows: 1 g Casamino acids (Difco Laboratories, Detroit, MI), 6 g $Na_2HPO_4$, 3 g $KH_2PO_4$, 0.5 g NaCl, 1 g $NH_4Cl$ is added to one liter milli-Q water (Millipore Corp., Bedford, Mass.), the pH adjusted to 7.4 and the solution autoclaved. The cooled medium is made 2 mM $MgSO_4$, 0.1 mM $CaCl_2$, and 0.2% glucose. After a 100-fold dilution of an overnight culture in M9CA supplemented with antibiotics, the cells were grown at 30° C. to A550 of 0.4, harvested by centrifugation, and stored as pellets at −20° C.

MAL Expression System: The tac promoter was induced with the gratuitous inducer IPTG. Overnight cultures were diluted 100-fold in LB medium supplemented with antibiotics, and the cells grown at 37° C. to $A_{550}$ of 0.4. IPTG was then added to a final concentration of 0.3 mM, and the bacteria incubated an additional 2 hr. The cells were then harvested by centrifugation and stored as pellets at −20° C.

Detection of AFP Expressed in E. Coli

Analytical studies were performed to determine the expression and behavior of recombinant AFP. Cell pellets were either suspended in SDS-lysis solution (0.16M Tris-HCl pH [6.8], 4% w/v SDS, 0.2M DTT, 20% glycerol, 0.02% bromophenol blue), boiled for 5 min, and used for analysis by SDS-PAGE or suspended in a lysis buffer consisting of 10 mM $Na_2HPO_4$, 30 mM NaCl, 0.25% Tween 20, 10 mM EDTA, 10 mM EGTA and incubated with 1 mg/ml lysozyme at 4° C. for 30 min prior to sonication in pulse mode for 3×1 min at 50% power (Sonics and Materials, Danbury, Conn.: model VC300 sonifier). The lysate was centrifuged at 10,000g for 20 min, and the supernatant containing soluble protein was decanted in a separate test tube and frozen at −20° C. until used. The pellet containing insoluble protein was resuspended in SDS-lysis buffer, boiled for 5 min and kept at −20° C. until used. Total protein released in SDS-lysis buffer, as well as soluble and pellet fractions were analyzed by SDS-PAGE and immunological detection following western blot transfer. In these studies coomassie blue stained gels were routinely scanned with a video densitometer (BioRad, model 620). This allowed a qualitative assessment of the amount of recombinant AFP produced as a percentage of total cellular protein.

Purification of AFP Expressed in the TRP System

All procedures were carried out at 4° C., unless otherwise stated. Each frozen cell pellet from a one liter culture was resuspended in 25 ml of lysis buffer A, 50 mM Tris-HCl [pH 7.5], 20% sucrose, 100 μg/ml lysozyme, 10 μg/ml PMSF), and incubated for 10 min. EDTA was added to a final concentration of 35 mM, and the extract allowed to stand a further 10 min. Following the addition of 25 ml of lysis buffer B (50 mM Tris-HCl [pH 7.5], 25 mM EDTA, 0.2% Triton X-100), the lysate was incubated an additional 30 min. The cell lysate was centrifuged at 12,000g for 20 min, and the precipitate containing the recombinant AFP was washed twice with 50 ml of wash buffer (50 mM Tris-HCl [pH 8.0], 10 mM EDTA, 0.2% Triton X-100), followed each time by centrifugation as above. The precipitate was dissolved in 50 ml of denaturation buffer (0.1M $K_2HPO_4$ [pH 8.5], 6M guanidine-HCl, 0.1M 2-mercaptoethanol), sonicated, and then mixed on a Nutator (Clay Adams) for 4 hr. The solubilized extract was diluted 50-fold in 50 mM Tris-HCl, 100 mM NaCl, 1 mM EDTA, and the recombinant AFP protein allowed to renature for 24 hr. This 50-fold dilution step is important because prior to dilution AFP appears to be microaggregated. Subsequent to dilution and reconcentration, AFP is not aggregated. The solution was concentrated 100-fold on YM10 membranes using an Amicon filtration unit, and clarified through a Millex 0.22 μm membrane filter (Millipore). The recombinant AFP was further purified at room temperature on a Mono Q column (Pharmacia) equilibrated in 20 mM Tris-HCl (pH 8.0) with bound proteins eluted using a linear gradient of 0–100% 1M NaCl, 20 mM Tris-HCl (pH 8.0). Fractions were analyzed by SDS-PAGE, APAGE, and Western blotting.

Polyacrylamide Gel Electrophoresis and Western Immunodetection Procedures

SDS-PAGE in discontinuous buffer system and alkaline-PAGE were performed according to Hames et al. (Gel Electrophoresis of Proteins: A Practical Approach, IRL Press, London, 1981) using the mini-Protean electrophoresis apparatus (BioRad). Immunological detection of recombinant human AFP following SDS-PAGE or APAGE was accomplished by soaking the gels in transfer buffer (12.5 mM Tris-HCl, 96 mM glycine, 20% methanol [pH 8.2]) for 15 min. Individual gels were then layered with an Immobilon PVDF membrane (Millipore) and sandwiched between the two electrode grids of the mini-Protean transfer device (BioRad), with the gels adjacent to the cathode. The system was immersed in transfer buffer, and a 150 mA current was applied for 2 hr. Unreacted sites on the Immobilon PVDF sheets were blocked in 20 mM Tris-HCl (pH 7.5), 500 mM NaCl, 3% gelatin for 1 hr. Rabbit anti-human AFP antiserum and goat anti-rabbit IgG antibodies conjugated to alkaline phosphatase (BioRad) were used as the primary and the secondary antibodies, respectively. The alkaline phosphatase activity was detected using 5-brome-4-chloro-3-indolyl phosphate and pnitroblue tetrazolium (Bio-Rad).

Quantitation of AFP Expression

Recombinant human AFP was quantitated using a human AFP ELISA kit (Abbott Laboratories, Chicago, Ill.).

AFP yield was estimated by scanning silver stained gels. When SG935 cells are transformed with the AFP encoding plasmid that employs the Trp expression system, AFP represents 2 to 5% of total cellular E. coli protein (approximately 3–7 mg AFP per liter of culture). As described above, most AFP in the initial extract is insoluble. The above-described resolubilization procedure permits 50–60% recovery of AFP in the form of stable, semi-purified, monomeric AFP (approximate yield 50 mg/20 l of E. coli). This can be further purifid to yield 25 mg of pure monomeric AFP.

N-Terminal Analysis

Automatic Edman degradations were performed using a Porton protein/peptide gas phase microsequencer with an integrated customized microbore HPLC to optimize sequence. Protein sequence analysis was aided by the use of selected programs within the PC/Gene software package (Intelligenetics).

Use

Recombinant human AFP and fragments thereof produced by procarkotic cells can be used for diagnostic standards and for therapeutic use.

Recombinant AFP and fragments thereof can be administered in an effective amount either alone or in combination with a pharmaceutically acceptable carrier or diluent. The polypeptides and compositions can be administered alone or in combination with other therapeutic agents by any convenient means, e.g., intravenously, orally, intramuscularly, or intranasally.

We claim:

1. A method of using a prokaryotic cell for producing biologically active human alpha-fetoprotein unfused to additional amino acids comprising providing a transformed prokaryotic cell comprising a recombinant DNA molecule encoding said human alpha-fetoprotein operably linked to an expression control element which directs the expression of said human alpha-fetoprotein, and culturing said transformed cell and purifying said alpha-fetoprotein wherein said alpha-fetoprotein is treated with a solubilizing agent, and then renatured to produce said biologically active alpha fetoprotein.

2. The method of claim 1 wherein said prokaryotic cell is *E. coli*.

3. The method of claim 1 wherein said expression control element comprises an *E. coli* Trp promoter.

4. The method of claim 1 wherein said expression control element comprises an *E. coli* Tac promoter.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO: 1:

TGTCTGCAGG ATGGGGAAAA A                                    2 1

( 2 ) INFORMATION FOR SEQ ID NO: 2:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 2:

CATGAAATGA CTCCAGTA                                      1 8

( 2 ) INFORMATION FOR SEQ ID NO: 3:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CATAGAAATG AATATGGA                                      1 8